United States Patent
Vijayakumari et al.

(10) Patent No.: US 9,012,694 B2
(45) Date of Patent: Apr. 21, 2015

(54) PROCESS FOR THE PRODUCTION OF ALCOHOLS

(71) Applicant: Shell Oil Company, Houston, TX (US)

(72) Inventors: Sivakumar Sadasivan Vijayakumari, Amsterdam (NL); Jeroen Van Westrenen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 14/368,569

(22) PCT Filed: Dec. 21, 2012

(86) PCT No.: PCT/EP2012/076848
§ 371 (c)(1),
(2) Date: Jun. 25, 2014

(87) PCT Pub. No.: WO2013/098272
PCT Pub. Date: Jul. 4, 2013

(65) Prior Publication Data
US 2015/0045586 A1    Feb. 12, 2015

(30) Foreign Application Priority Data

Dec. 27, 2011 (EP) .................................... 11195830

(51) Int. Cl.
C07C 45/50 (2006.01)
C07C 29/16 (2006.01)
C07C 1/20 (2006.01)
C07C 29/14 (2006.01)
C07C 1/22 (2006.01)
C07C 4/06 (2006.01)

(52) U.S. Cl.
CPC ................. *C07C 45/50* (2013.01); *C07C 29/14* (2013.01); *C07C 1/22* (2013.01); *C07C 4/06* (2013.01)

(58) Field of Classification Search
CPC .......... C07C 45/50; C07C 29/16; C07C 1/20; C07C 1/22; C07C 2529/40
USPC .................... 568/451, 882, 883; 585/310, 642
See application file for complete search history.

(56) References Cited

U.S. PATENT DOCUMENTS

| | | |
|---|---|---|
| 3,369,050 A | 2/1968 | Green |
| 3,420,898 A | 1/1969 | Van Winkle et al. |
| 3,440,291 A | 4/1969 | Van Winkle et al. |
| 3,448,157 A | 6/1969 | Slaugh et al. |
| 3,448,158 A | 6/1969 | Slaugh et al. |
| 3,501,515 A | 3/1970 | Van Winkle et al. |
| 4,567,029 A | 1/1986 | Wilson et al. |
| 2007/0155999 A1 | 7/2007 | Pujado et al. |
| 2007/0203380 A1 | 8/2007 | Vora et al. |

FOREIGN PATENT DOCUMENTS

| | | |
|---|---|---|
| DE | 102006060610 | 6/2008 |
| WO | 2005058782 | 6/2005 |
| WO | 2006020083 | 2/2006 |
| WO | 2011087690 | 7/2011 |

*Primary Examiner* — Sikarl Witherspoon

(57) ABSTRACT

The present invention provides a process for the production of aldehydes and/or alcohols, which process comprises the steps of: (a) reacting an oxygenate and/or olefinic feed in a reactor in the presence of a molecular sieve catalyst to form an effluent comprising olefins, comprising propylene; (b) separating the effluent comprising olefins as obtained in step (a) into at least a first olefinic product fraction comprising propylene and a second olefinic product fraction; (c) subjecting at least part of the first olefinic product fraction as obtained in step (b) to a hydroformylation process to form aldehydes; (d) separating at least part of the aldehydes as obtained in step (c) into at least a first product fraction of aldehydes and a second product fraction of aldehydes; and (e) hydrogenating at least part of the aldehydes in the first and/or second product fraction of aldehydes as obtained in step (d) to form a first product fraction of alcohols and/or a second product fraction of alcohols; (f) recycling at least part of the first and/or second product fraction of alcohols obtained in step (e) to step (a).

15 Claims, No Drawings

PROCESS FOR THE PRODUCTION OF ALCOHOLS

PRIORITY CLAIM

The present application is the National Stage (§371) of International Application No. PCT/EP2012/076848, filed Dec. 21, 2012, which claims priority from European patent application no. 11195830.2, filed Dec. 27, 2011, the disclosures of which are incorporated herein by reference.

FIELD OF THE INVENTION

This invention relates to a process for the production of alcohols.

BACKGROUND OF THE INVENTION

Various processes for producing aldehyde and/or alcohol compounds by the reaction of an olefin with carbon monoxide and hydrogen in the presence of a catalyst are known. Typically, these reactions are performed at elevated temperatures and pressures. The aldehyde and alcohol compounds that are produced generally correspond to compounds obtained by the addition of a carbonyl or carbinol group, respectively, to an unsaturated carbon atom in the starting material with simultaneous saturation of the unsaturated carbon-carbon bond. Isomerization of the olefin bond may take place to varying degrees under certain conditions; thus, as a consequence of this isomerization, a variety of products may be obtained. These processes are typically known as hydroformylation reactions.

The catalyst employed in a hydroformylation reaction typically comprises a transition metal, such as cobalt, platinum, rhodium or ruthenium, in complex combination with carbon monoxide and ligand(s) such as an organophosphine.

The following documents are representative of the earlier hydroformylation methods which use transition metal catalysts: U.S. Pat. No. 3,420,898, U.S. Pat. No. 3,501,515, U.S. Pat. No. 3,448,157, U.S. Pat. No. 3,440,291, U.S. Pat. No. 3,369,050 and U.S. Pat. No. 3,448,158.

As mentioned above, several products may be obtained. In case of for instance the hydroformylation of propylene, a mixture of normal butyraldehyde and iso-butyraldehyde may be formed, which through a subsequent hydrogenation may be converted to a mixture of normal butyl-alcohol and isobutyl-alcohol. In attempts to improve the selectively of the hydroformylation reaction toward either normal butyraldehyde and iso-butyraldehyde, attention has typically focussed on developing novel catalysts and novel processes for recovering and re-using the catalyst. In particular, novel catalysts have been developed which may exhibit improved selectively toward normal butyraldehyde and optionally normal butyl-alcohol. In WO 2011/087690 A1 a hydroformylation process is described using a rhodium based catalyst comprising at least two different ligand molecules. According to WO 2011/087690 A1 the use of the two different ligand molecules may provide a higher normal butyraldehyde over iso-butyraldehyde ratio.

A disadvantage of the process of WO 2011/087690 A1 is that it requires two different ligand molecules, which makes the catalyst system and accompanying process complex and expensive.

There is a need for a process to produce aldehydes and/or alcohols at a high normal over iso-aldehydes or alcohol ratio or a high iso over normal aldehydes or alcohol ratio, without the need to use complex hydroformylation catalyst(s).

SUMMARY OF THE INVENTION

According to the present invention there is provided a process for the production of aldehydes and/or alcohols, which process comprises the steps of:
(a) reacting an oxygenate and/or olefinic feed in a reactor in the presence of a molecular sieve catalyst to form an effluent comprising olefins, comprising propylene;
(b) separating the effluent comprising olefins as obtained in step (a) into at least a first olefinic product fraction comprising propylene and a second olefinic product fraction;
(c) subjecting at least part of the first olefinic product fraction as obtained in step (b) to a hydroformylation process to form aldehydes;
(d) separating at least part of the aldehydes as obtained in step (c) into at least a first product fraction of aldehydes and a second product fraction of aldehydes; and
(e) hydrogenating at least part of the aldehydes in the first and/or second product fraction of aldehydes as obtained in step (d) to form a first product fraction of alcohols and/or a second product fraction of alcohols;
(f) recycling at least part of the first and/or second product fraction of alcohols obtained in step (e) to step (a).

In accordance with the present invention a highly effective and efficient integrated process is provided for the production of aldehydes and/or alcohols.

Preferably, the first product fraction of aldehydes as obtained in step (d) comprises isobutyl-aldehydes and the second product fraction of aldehydes as obtained in step (d) comprises normal butyl-aldehydes, while first product fraction of alcohols as obtained in step (e) comprises isobutyl-alcohol and the second product fraction of alcohols as obtained in step (e) comprises normal butyl-alcohol.

A major advantage of the present process is that a high selectivity towards normal butyraldehydes and normal butyl-alcohols can be established without requiring an expensive catalyst system, and that the iso-butyraldehyde to normal butyraldehyde ratio, respectively the isobutyl-alcohol to normal butyl-alcohol ratio can be adjusted to meet market demands.

If desired, it is possible to recycle normal butyl-alcohol, obtained by the hydrogenation of normal butyl aldehyde, to step (a) rather than the isobutyl-alcohol, obtained by the hydrogenation of isobutyl aldehyde. In that case, isobutyl aldehyde, respectively isobutyl-alcohol may be retrieved as a product.

A further advantage of the process according to the invention is that the butanol, normal butyl-alcohol or isobutyl-alcohol, recycled to step (a) is at least in part converted back to propylene, which can be provided as part of the first olefinic fraction to prepare further alcohols.

Suitably, at least part of the first product fraction of alcohols, preferably comprising isobutyl-alcohol, is recycled to step (a). Preferably, the entire first product fraction of alcohols is recycled to step (a).

Suitably, at least part of the second olefinic product fraction which may comprise normal butyl-alcohol as obtained in step (e) is recycled to step (a).

Preferably, the second olefinic product fraction as obtained in step (b) is an olefinic product fraction comprising olefins have 4 or more carbon atoms. Preferably, at least part of the second olefinic product fraction as obtained in step (b) is subjected to an separate olefin cracking process to convert at least part of the olefins comprising 4 or more carbon atoms to olefins having a lower carbon number, i.e. an olefin having n carbon atoms is cracked to at least one olefin have m carbon atoms, wherein n and m are integers and m is smaller than n. Preferably, the olefins comprising 4 or more carbon atoms are cracked to at least ethylene and propylene. At least part of the olefins thus formed is recycled to step (b).

Preferably, at least part of the second olefinic product fraction comprising olefins having 4 or more carbon atoms as obtained in step (b) is first fractionated to obtain at least a third olefinic product fraction comprising C4 olefins and a fourth olefinic product fraction comprising olefins having 5 or more carbon atoms, wherein at least part of the fourth fraction is provided to the separate olefin cracking process, while at least part of the third olefinic product fraction is recycled as recycle stream to step (a).

The effluent comprising olefins as obtained in step (a) may also comprise ethylene in addition to propylene. Ethylene is a valuable chemical feedstock. It is an advantage of the present invention that the alcohol, preferably butanol, which is recycled back to step (a) may at least in part be converted to further ethylene. As such part of the obtained effluent in step (a) is converted to ethylene.

Preferably, the first olefinic product fraction as obtained in step (b) mainly contains propylene.

DETAILED DESCRIPTION OF THE INVENTION

In the present invention, an oxygenate feed is converted in an oxygenate-to-olefins (OTO) process and/or an olefinic feed is converted in an olefin cracking process (OCP).

The present invention in particularly relates to a process for the conversion of oxygenates into olefins.

In step (a), an oxygenate feed and/or olefinic feed is reacted in a reactor in the presence of a molecular sieve catalyst to form a effluent which comprises olefins and at least partially coked catalyst. The reactor in step (a) can be an OTO reaction zone wherein at least the oxygenate feed is contacted with an oxygenate conversion catalyst under oxygenate conversion conditions, to obtain a conversion effluent comprising lower olefins. Reference herein to an oxygenate feed is to an oxygenate-comprising feed. In the OTO reaction zone, at least part of the feed is converted into a product containing one or more olefins, preferably including lower olefins, in particular ethylene and propylene.

The oxygenate used in the process according to the invention is preferably an oxygenate which comprises at least one oxygen-bonded alkyl group. The alkyl group preferably is a C1-C5 alkyl group, more preferably C1-C4 alkyl group, i.e. comprises 1 to 5, respectively, 4 carbon atoms; more preferably the alkyl group comprises 1 or 2 carbon atoms and most preferably one carbon atom. Examples of oxygenates that can be used in the oxygenate feed include alcohols and ethers. Examples of preferred oxygenates include alcohols, such as methanol, ethanol, propanol; and dialkyl ethers, such as dimethylether, diethylether, methylethylether. Preferably, the oxygenate is methanol or dimethylether, or a mixture thereof. More preferably, the oxygenate feed comprises methanol or dimethylether.

Preferably the oxygenate feed comprises at least 50 wt % of oxygenate, in particular methanol and/or dimethylether, based on total hydrocarbons, more preferably at least 70 wt %.

The oxygenate feed can comprise an amount of diluent, such as nitrogen and water, preferably in the form of steam. In one embodiment, the molar ratio of oxygenate to diluent is between 10:1 and 1:10, preferably between 4:1 and 1:2, in particular when the oxygenate is methanol and the diluent is water (steam).

A variety of OTO processes is known for converting oxygenates such as for instance methanol or dimethylether to an olefin-containing product, as already referred to above. One such process is described in WO-A 2006/020083. Processes integrating the production of oxygenates from synthesis gas and their conversion to light olefins are described in US20070203380A1 and US20070155999A1.

Catalysts suitable for converting the oxygenate feed in accordance with the present invention include molecular sieve-catalysts. The molecular sieve catalyst suitably comprises one or more zeolite catalysts and/or one or more SAPO catalysts. Molecular sieve catalysts typically also include binder materials, matrix material and optionally fillers. Suitable matrix materials include clays, such as kaolin. Suitable binder materials include silica, alumina, silica-alumina, titania and zirconia, wherein silica is preferred due to its low acidity.

Molecular sieve catalysts preferably have a molecular framework of one, preferably two or more corner-sharing [$TO_4$] tetrahedral units, more preferably, two or more [$SiO_4$], [$AlO_4$] and/or [$PO_4$] tetrahedral units. These silicon, aluminum and/or phosphorous based molecular sieves and metal containing silicon, aluminum and/or phosphorous based molecular sieves have been described in detail in numerous publications including for example, U.S. Pat. No. 4,567,029. In a preferred embodiment, the molecular sieve catalysts have 8-, 10- or 12-ring structures and an average pore size in the range of from about 3 Å to 15 Å.

Suitable molecular sieve catalysts are silicoaluminophosphates (SAPO), such as SAPO-17, -18, -34, -35, -44, but also SAPO-5, -8, -11, -20, -31, -36, -37, -40, -41, -42, -47 and -56; aluminophosphates (AlPO) and metal substituted (silico)aluminophosphates (MeAlPO), wherein the Me in MeAlPO refers to a substituted metal atom, including metal selected from one of Group IA, IIA, IB, IIIB, IVB, VB, VIB, VIIB, VIIIB and Lanthanide's of the Periodic Table of Elements, preferably Me is selected from one of the group consisting of Co, Cr, Cu, Fe, Ga, Ge, Mg, Mn, Ni, Sn, Ti, Zn and Zr.

Preferably, the conversion of the oxygenate feed may be accomplished by the use of an aluminosilicate-comprising catalyst, in particular a zeolite-comprising catalyst. In a zeolite-comprising catalyst the amount of zeolite is suitably from 20 to 50 wt %, preferably from 35 to 45 wt %, based on total catalyst composition.

Suitable catalysts include those containing a zeolite of the ZSM group, in particular of the MFI type, such as ZSM-5, the MTT type, such as ZSM-23, the TON type, such as ZSM-22, the MEL type, such as ZSM-11, the FER type. Other suitable zeolites are for example zeolites of the STF-type, such as SSZ-35, the SFF type, such as SSZ-44 and the EU-2 type, such as ZSM-48.

Aluminosilicates-comprising catalyst, and in particular zeolite-comprising catalyst are preferred when an olefinic co-feed is fed to the oxygenate conversion zone together with oxygenate, for increased production of ethylene and propylene.

Preferred catalysts comprise a more-dimensional zeolite, in particular of the MFI type, more in particular ZSM-5, or of the MEL type, such as zeolite ZSM-11. Such zeolites are particularly suitable for converting olefins, including iso-olefins, to ethylene and/or propylene. The zeolite having more-dimensional channels has intersecting channels in at least two directions. So, for example, the channel structure is formed of substantially parallel channels in a first direction, and substantially parallel channels in a second direction, wherein channels in the first and second directions intersect. Intersections with a further channel type are also possible. Preferably, the channels in at least one of the directions are 10-membered ring channels. A preferred MFI-type zeolite has a Silica-to-Alumina ratio (SAR) of at least 60, preferably at least 80.

Particular catalysts may include catalysts comprising one or more zeolite having one-dimensional 10-membered ring channels, i.e. one-dimensional 10-membered ring channels, which are not intersected by other channels. Preferred examples are zeolites of the MTT and/or TON type.

In a preferred embodiment the catalyst comprises in addition to one or more one-dimensional zeolites having 10-membered ring channels, such as of the MTT and/or TON type, a more-dimensional zeolite, in particular of the MFI type, more in particular ZSM-5, or of the MEL type, such as zeolite ZSM-11.

The catalyst may comprise phosphorus as such or in a compound, i.e. phosphorus other than any phosphorus included in the framework of the molecular sieve. It is preferred that an MEL or MFI-type zeolites comprising catalyst additionally comprises phosphorus. The phosphorus may be introduced by pre-treating the MEL or MFI-type zeolites prior to formulating the catalyst and/or by post-treating the formulated catalyst comprising the MEL or MFI-type zeolites. Preferably, the catalyst comprising MEL or MFI-type zeolites comprises phosphorus as such or in a compound in an elemental amount of from 0.05-10 wt % based on the weight of the formulated catalyst. A particularly preferred catalyst comprises phosphorus and MEL or MFI-type zeolites having SAR of in the range of from 60 to 150, more preferably of from 80 to 100. An even more particularly preferred catalyst comprises phosphorus and ZSM-5 having SAR of in the range of from 60 to 150, more preferably of from 80 to 100.

It is preferred that the molecular sieves in the hydrogen form are used in the oxygenate conversion catalyst, e.g., HZSM-22, HZSM-23, and HZSM-48, HZSM-5. Preferably at least 50% w/w, more preferably at least 90% w/w, still more preferably at least 95% w/w and most preferably 100% of the total amount of molecular sieve used is in the hydrogen form. It is well known in the art how to produce such molecular sieves in the hydrogen form.

The catalyst particles used in the process of the present invention can have any shape known to the skilled person to be suitable for this purpose, for it can be present in the form of spray dried catalyst particles, spheres, tablets, rings, extrudates, etc. Extruded catalysts can be applied in various shapes, such as, cylinders and trilobes. Spherical particles are normally obtained by spray drying. Preferably the average particle size is in the range of 1-500 µm, preferably 50-100 µm.

The reaction conditions of the oxygenate conversion in step (a) include a reaction temperature from 350 to 750° C., preferably from 450 to 750° C., more preferably from 450 to 700° C., even more preferably 500 to 650° C.; and a pressure of from 1-15 bara, preferably from 1-4 bara, more preferably from 1.1-3 bara, and even more preferably from 1.3-2 bara.

Suitably, the oxygenate-comprising feed is preheated to a temperature in the range of from 120 to 550° C., preferably 250 to 500° C. prior to contacting with the molecular sieve catalyst in step (a).

Preferably, in addition to the oxygenate, an olefinic co-feed is provided along with and/or as part of the oxygenate feed. Reference herein to an olefinic co-feed is to an olefin-comprising co-feed. The olefinic co-feed preferably comprises C4 and higher olefins, more preferably C4 and C5 olefins. Preferably, the olefinic co-feed comprises at least 25 wt %, more preferably at least 50 wt %, of C4 olefins, and at least a total of 70 wt % of C4 hydrocarbon species. The olefinic co-feed can also comprise propylene.

The reaction in step (a) may suitably be operated in a fluidized bed, e.g. a dense, turbulent or fast fluidized bed or a riser reactor or a downward reactor system, and also in a fixed bed reactor, moving bed or a tubular reactor. A fluidized bed, e.g. a turbulent fluidized bed, fast fluidized bed or a riser reactor system are preferred. These could be arranged as a single or multiple reactors in parallel or in series.

The superficial velocity of the gas components in a dense fluidized bed will generally be from 0 to 1 m/s; the superficial velocity of the gas components in a turbulent fluidized bed will generally be from 1 to 3 m/s; the superficial velocity of the gas components in a fast fluidized bed will generally be from 3 to 5 m/s; and the superficial velocity of the gas components in a riser reactor will generally be from 5 to about 25 m/s.

It will be understood that dense, turbulent and fast fluidized beds will include a dense lower reaction zone with densities generally above 300 kg/m$^3$. Moreover, when working with a fluidized bed several possible configurations can be used: (a) co-current flow meaning that the gas (going upward) and the catalyst travels through the bed in the same direction, and (b) countercurrent, meaning that the catalyst is fed at the top of the bed and travels through the bed in opposite direction with respect to the gas, whereby the catalyst leaves the vessel at the bottom. In a conventional riser reactor system the catalyst and the vapors will travel co-currently.

More preferably, a fluidized bed, in particular a turbulent fluidized bed system is used. Suitably, in such a moving bed reactor the oxygenate feed is contacted with the molecular sieve catalyst at a weight hourly space velocity of at least 1 hr$^{-1}$, suitably from 1 to 1000 hr$^{-1}$, preferably from 1 to 500 hr$^{-1}$, more preferably 1 to 250 hr$^{-1}$, even more preferably from 1 to 100 hr$^{-1}$, and most preferably from 1 to 50 hr$^{-1}$.

The reactor in step (a) can also be an OCP reaction zone wherein the olefinic feed is contacted with an zeolite-comprising catalyst under olefin conversion conditions.

Suitably, the olefinic feed comprises C4+ olefins that are converted by contacting such a feed with a zeolite-comprising catalyst, thereby converting at least part of the olefins comprising 4 or more carbon atoms to olefins having a lower carbon number, i.e. a olefin having n carbon atoms is cracked to at least one olefin have m carbon atoms, wherein n and m are integers and m is smaller than n. Preferably, the olefins comprising 4 or more carbon atoms are cracked to at least ethylene and propylene.

Preferably, the olefinic feed is contacted with the zeolite-comprising catalyst in step (a) at a reaction temperature of 350 to 1000° C., preferably from 375 to 750° C., more preferably 450 to 700° C., even more preferably 500 to 650° C.; and a pressure from 1 bara to 50 bara, preferably from 1-15 bara. Optionally, such olefinic feed also contains a diluent. Examples of suitable diluents include, but are not limited to, such as water or steam, nitrogen, paraffins and methane. Under these conditions, at least part of the olefins in the olefinic feed are converted to further ethylene and/or propylene.

In an OCP suitably aluminosilicate catalysts are used. Aluminosilicate catalysts, and in particular zeolite catalysts, have the additional advantage that in addition to the conversion of methanol or ethanol, these catalysts also induce the conversion of olefins to ethylene and/or propylene. Therefore, aluminosilicate catalysts, and in particular zeolite catalysts, are particularly suitable for use as the catalyst in an OCP unit.

The preferences provided herein above for the oxygenate to olefins catalyst apply mutatis mutandis for the OCP catalyst with the primary exception that the OCP catalyst always comprises at least one zeolite.

Particular preferred catalysts for the OCP reaction, i.e. converting part of the olefinic product, and preferably part of the C4+ hydrocarbon fraction of the olefinic product including olefins, are catalysts comprising at least one zeolite selected from MFI, MEL, TON and MTT type zeolites, more preferably at least one of ZSM-5, ZSM-11, ZSM-22 and ZSM-23 zeolites.

The catalyst may further comprise phosphorus as such or in a compound, i.e. phosphorus other than any phosphorus included in the framework of the molecular sieve. It is preferred that a MEL or MFI-type zeolite comprising catalyst additionally comprises phosphorus. The phosphorus may be introduced by pre-treating the MEL or MFI-type zeolites prior to formulating the catalyst and/or by post-treating the formulated catalyst comprising the MEL or MFI-type zeolites. Preferably, the catalyst comprising MEL or MFI-type zeolites comprises phosphorus as such or in a compound in an elemental amount of from 0.05 to 10 wt % based on the weight of the formulated catalyst. A particularly preferred catalyst comprises phosphorus and MEL or MFI-type zeolite having SAR of in the range of from 60 to 150, more preferably of from 80 to 100. An even more particularly preferred catalyst comprises phosphorus and ZSM-5 having SAR of in the range of from 60 to 150, more preferably of from 80 to 100.

Preferably, the oxygenate to olefins catalyst and the olefin cracking catalyst are the same zeolite-comprising catalyst.

Also an OCP process may suitably be operated in a fluidized bed, e.g. a fast fluidized bed or a riser reactor or a downward reactor system, and also in a fixed bed reactor, moving bed reactor or a tubular reactor. A fluidized bed, e.g. a fast fluidized bed or a riser reactor system are preferred.

The olefins and at least partially coked catalyst as obtained in step (a) will be separated. The separation can be carried out by one or more cyclone separators. Such one or more cyclone separators may be located inside, partly inside and partly outside, or outside the reactor used in step (a). Such cyclone separators are well known in the art. Cyclone separators are preferred, but also methods for separating the catalyst from the olefins can be used that apply plates, caps, elbows, and the like.

In step (b), the effluent comprising olefins as obtained in step (a) are separated into at least a first olefinic product fraction comprising propylene, and a second olefinic product fraction, preferably comprising olefins having 4 or more carbon atoms. Preferably, the first olefinic fraction comprises in the range of from 50 to 100 wt %, more preferably of from 80 to 100 wt %, even more preferably 95 to 100 wt % of propylene, based on the hydrocarbons in the first olefinic product fraction. Suitably, at least part of the second olefinic product fraction is recycled to step (a) for use as an olefinic co-feed.

Preferably, at least 70 wt % of the olefinic co-feed, during normal operation, is formed by the recycle stream of the second olefinic product fraction containing olefins having 4 or more carbon atoms, preferably at least 90 wt % of olefinic co-feed, based on the whole olefinic co-feed, is formed by such a recycle stream.

In order to maximize production of ethylene and propylene, it is desirable to optimize the recycle of olefins having more than 4 carbon atoms in the effluent to the OTO or olefin cracking process. This can be done by recycling at least part of the second olefinic fraction containing olefins having 4 or more carbon atoms, preferably the C4-C5 hydrocarbon fraction, more preferably the C4 hydrocarbon fraction, to the OTO or OCP reaction zone in step (a). Suitably, however, a certain part thereof, such as between 1 and 5 wt %, is withdrawn as purge, since otherwise saturated hydrocarbons, in particular C4's (butane) would build up in the process, which are substantially not converted under the OTO or OCP reaction conditions.

The preferred molar ratio of oxygenate in the oxygenate feed to olefin in the olefinic co-feed provided to the OTO reaction zone in step (a) depends on the specific oxygenate used and the number of reactive oxygen-bonded alkyl groups therein. Preferably the molar ratio of oxygenate to olefin in the total feed lies in the range of 20:1 to 1:10, more preferably in the range of 18:1 to 1:5, still more preferably in the range of 15:1 to 1:3, even still more preferably in the range of 12:1 to 1:3.

Although the second olefinic fraction containing olefins having 4 or more carbon atoms as separated from the effluent comprising olefins as recovered in step (b) may be recycled as an olefinic co-feed to the OTO reaction zone in step (a), alternatively at least part of the olefins in the second olefinic fraction may be converted to ethylene and/or propylene by contacting such C4+ hydrocarbon fraction in a separate olefin cracking unit with a zeolite-comprising catalyst. This is particularly preferred when the molecular sieve catalyst in step (a) comprises a least one SAPO, AlPO, or MeAlPO type molecular sieve, preferably SAPO-34. These catalysts are less suitable for converting olefins. Preferably, the C4+ hydrocarbon fraction is contacted with the zeolite-comprising catalyst at a reaction temperature of 350 to 1000° C., preferably from 375 to 750° C., more preferably 450 to 700° C., even more preferably 500 to 650° C.; and a pressure from 1 bara to 50 bara, preferably from 1-15 bara. Optionally, such a stream comprising C4+ olefins also contains a diluent. Examples of suitable diluents include, but are not limited to, such as water or steam, nitrogen, and methane. Under these conditions, at least part of the olefins in the C4+ hydrocarbon fraction are converted to further ethylene and/or propylene. The further ethylene and/or propylene may be combined with the ethylene and/or propylene as obtained in step (b). Such a separate process step directed at converting C4+ olefins to ethylene and propylene is, as will be clear from the foregoing, also referred to as an olefin cracking process (OCP).

In such a subsequent separate OCP suitably zeolite-comprising catalysts are used. Catalyst suitable for an olefin cracking process have been described herein above and may be used for the additional separate OCP process step.

Preferably, the catalyst used in step (a) and the separate OCP unit are the same zeolite-comprising catalyst.

Preferably, at least part of the second olefinic product fraction comprising olefins having 4 or more carbon atoms as obtained in step (b) is first fractionated to obtain at least a third olefinic product fraction comprising C4 olefins and a fourth olefinic product fraction comprising olefins having 5 or more carbon atoms, wherein at least part of the fourth fraction is provided to the separate olefin cracking unit, while at least part of the third olefinic product fraction is recycled as recycle stream to step (a). By converting the olefins having 5 or more carbon atoms separately in the separate OCP unit, the condition in the separate OCP unit can be selected to obtain an optimal converse of olefins having more than 5 carbon atoms.

At least partially coked catalyst as obtained in step (a) can be passed to a regenerator. Suitably, the at least partially coked catalyst as obtained in step (a) is passed in its entirety or a portion of it to the regenerator. The molecular sieve catalyst to be used in accordance with the present invention deactivates in the course of the process with time, due to issues around coke deposition and hydrothermal stability.

Hence, the molecular sieve catalyst needs to be regenerated in order to at least partly remove coke from the coked catalyst as obtained in step (a). Conventional catalyst regeneration techniques can be employed to remove the coke. It is not necessary to remove all the coke from the catalyst as it is believed that a preset amount of residual coke may enhance the catalyst performance and additionally, it is believed that complete removal of the coke may also lead to degradation of the molecular sieve.

In order to regenerate at least part of the at least partially coked catalyst an oxygen-containing gas will be introduced in the regenerator, thereby producing a gaseous mixture and at least partially regenerated catalyst. The oxygen-containing gas may be chosen from oxygen and air. Also mixtures can suitably be used of these oxygen-containing gases. Preferably, the oxygen-containing gas comprises oxygen, more preferably air is used as the oxygen-containing gas.

The regeneration will be carried out under conditions of temperature, pressure and residence time that is usually applied in regeneration processes to burn coke from catalysts. Suitably, between 0.01-5 wt % of the coke present on the at least partially coked catalyst is removed from the catalyst during regeneration.

Suitably, the regeneration is carried out at a temperature in the range of from 580-800° C., preferably in the range of from 600-750° C., more preferably in the range of from 620-680° C., and a pressure in the range of from 1-5 bara, preferably in the range of from 1-3 bara, more preferably in the range of from 1.3-2 bara. The regeneration can suitably be carried out in a fixed bed, a fluidized bed such as a dense, turbulent or fast fluidized bed or in a riser or downward regenerator. Preferably, the regeneration is carried out in a turbulent fluidized bed.

Suitably, the regeneration can be carried out in a periodical manner or continuous manner. Preferably, the regeneration is carried out in a continuous manner.

The hydroformylation process to be used in step (c) can be any known hydroformylation process. In a hydroformylation process, an olefin is converted in the presence of a catalyst with carbon monoxide and hydrogen to an aldehyde having at least one carbon atom more than the olefin. For instance, propylene may be converted to butyraldehyde in a hydroformylation process.

In the hydroformylation process preferably use is made of catalyst which comprises a transition metal in complex combination ligand(s), such as an organophosphine and/or organophosphate, and optionally carbon monoxide. Suitable transition metals that can be used in step (c) include rhodium, cobalt, iridium, ruthenium, iron, nickel, palladium, platinum, osmium and any mixture thereof. Preferred transition metals are rhodium, cobalt, iridium and ruthenium, more preferably rhodium, cobalt and ruthenium, and most preferably rhodium.

Suitably, a hydrogen to carbon monoxide molar ratio is used in range of from 1:10 to 100:1, preferably in the range of from 1:10 to 10:1.

In accordance with the present invention the molar ratio of hydrogen to carbon monoxide in the hydroformylation process, wherein the intended product is an alcohol, is preferably in the range of from 2.5:1 to 1:2.5, more preferably in the range of from 2.2:1 to 1:2.2

Suitably, water is added into the reactor system to be used in the hydroformylation process.

The hydroformylation process of the present invention may be carried out as a batch process or as a continuous process.

The hydroformylation process in step (c) can suitably be carried out in one or two or more reaction zones. The term "reaction zone", as used herein, refers to a controlled environment which contains the reaction mixture, wherein the hydroformylation process of the present invention may occur. A reaction zone can be, for example, a reactor or a section of a reactor in which the reaction conditions, including temperature, pressure and, optionally, concentration of reagents, may be controlled independently from the rest of the reactor. Typically, the reaction zones are reactors.

The number of reaction zones used in order to carry out the process of the present invention is not critical. When the reaction zones of the process of the present invention are reactors, the reactors may be isolated reactors or a series of reactors which are linked together. Preferably the process of the present invention is carried out in at least two reactors linked in series. By the term "linked in series" as used herein, it is meant a series of separate reaction zones which are linked together so as to form a continuous reaction chain where the reaction mixture passes continuously from one reaction zone to the next under controlled temperature and pressure conditions, wherein the temperature and pressure of the individual reaction zones may be set independently.

The hydrogen and carbon monoxide may be introduced into the process of the present invention as two distinct streams, i.e. a hydrogen gas feed stream and a carbon monoxide gas feed stream, or as a combined feed stream, e.g. a syngas feed stream. 'Syngas' as used herein refers to a mixture of carbon monoxide and hydrogen generated, for example, by the gasification of a carbon-containing fuel.

Commercially or industrially available combined hydrogen and carbon monoxide streams (e.g. syngas) can be used in the hydroformylation process in step (c). Generally such gas streams contain a ratio of hydrogen to carbon monoxide of greater than 1.65:1. Optionally, water is added to perform a Ni catalyzed water gas shift reaction to adjust the molar ratio of hydrogen to carbon monoxide. Optionally, $CO_2$ can be removed from the syngas before use in step (c). A suitable combined hydrogen/carbon monoxide feed stream may be provided by a method that reduces the level of hydrogen in the stream relative to the level of carbon monoxide in such a stream. This may involve adding carbon monoxide or removing hydrogen from the combined hydrogen and carbon monoxide stream. Hydrogen can be removed from a combined hydrogen and carbon monoxide stream by any suitable method, such as absorption or reaction.

In one embodiment of the present invention, a combined hydrogen/carbon monoxide feed stream is provided for the hydroformylation process by using a combined hydrogen/carbon monoxide feed stream which comprises a combined hydrogen/carbon monoxide feed stream which has already been used in a reaction that reduces the ratio of hydrogen to carbon monoxide in said combined gas feed stream. Preferably, the combined hydrogen/carbon monoxide stream has already been subjected to a hydroformylation reaction. More preferably, the combined hydrogen/carbon monoxide stream is a recycled stream from the hydroformylation process as carried out in step (c).

It will be understood by the skilled person that, as the reaction proceeds, the molar ratio of hydrogen to carbon monoxide will vary throughout the reaction environment. The ratio of hydrogen to carbon monoxide in the reaction environment may also vary if a further hydrogen gas feed stream and/or a combined hydrogen/carbon monoxide feed stream is introduced into a second and/or a later reaction zone(s).

The hydroformylation process in step (c) may be carried out over a wide range of temperatures. Suitable temperatures for the reaction environment are in the range of from 50 to 220° C., preferably in the range of from 80 to 180° C., more preferably in the range of from 90 to 140° C.

The hydroformylation process in step (c) may be carried out at various pressures. Consequently, hydroformylation in accordance with the process of the present invention may typically be carried out at pressures in the range of from 0.1-200 bar, preferably in the range of from 10-100 bar.

The product stream as obtained in step (c) will comprise aldehyde, catalyst, by-products and any unconsumed reactants. The product stream as obtained in step (c) may be subjected to suitable catalyst and product separating means comprising one or more steps, for example, stratification, solvent extraction, distillation, fractionation, adsorption, filtration, etc. The specific method of product and catalyst separation employed will be governed to some extent by the specific metal ion in complex combination with carbon monoxide and ligand(s) and reactants charged. Catalyst or components thereof, as well as unconsumed reactants, by-products, aldehyde products, and solvent, when employed, may be recycled in part or in their entirety to the hydroformylation process. For example, a part of an aldehyde reaction product may, if desired, be recycled to the hydroformylation process in step (c) to function as solvent and/or diluent and/or suspending medium for the catalyst and the catalyst components. Part of the heavy ends by-product as obtained in the hydroformylation process in step (c) may also be recycled to the reaction environment in order to aid solution and/or suspension of the catalyst. Further, part or all of any aldehyde produced, may optionally be recycled to the hydroformylation process, but preferably is subjected to hydrogenation conditions in a separate reaction environment in the presence of a metal-based hydrogenation catalyst In a preferred embodiment of the present invention, the used catalyst in the hydroformylation process is recycled to the reaction environment as a feed stream for re-use.

In a preferred embodiment of the present invention, before any addition of water, the stream to be recycled comprises at most 300 ppmw, more preferably at most 100 ppmw, even more preferably at most 50 ppmw, most preferably at most 20 ppmw of water.

Additional preformed catalyst, or separate components of the catalyst capable of producing the active complex in situ, may be added to the separated material which is being recycled to the reaction environment or alternatively to the product stream exiting the reaction environment before said product stream is subjected to separating means. Further, such preformed catalyst, or separate components of the catalyst capable of producing the active complex in situ, may be added directly to the reactor or into the olefinic feed stream to step (c).

The water is preferably added into the reaction system in an amount of at least 0.05 wt %, more preferably at least 0.075 wt %, most preferably at least 0.1 wt %, based on the total weight of the reaction mixture. The water is preferably added into the reaction system in an amount of at most 10 wt %, more preferably at most 5 wt %, most preferably at most 2 wt %, based on the total weight of the reaction mixture.

In a preferred embodiment, the hydroformylation process in step (c) is carried out as a continuous process and water is continually added into the reactor system in order to maintain the amount of water at the desired level. The water to be added into the reactor system may also be added to the reactor system as an aqueous solution of one or more salts. Suitable salts include, but are not limited to KOH, NaOH, NaSH and Na2S. The water may be added at any point in the reactor system. In one embodiment of the present invention, the water is added at the beginning of the reactor system. In order to achieve this, the water may be added into the reaction environment as a separate feed stream or it may be added to one of the feed streams containing one or more of the other reactants. For example, the water may be added to the recycled catalyst feed stream. Alternatively, it may be preferable to add the water to a feed stream comprising olefinic feedstock or into a feed stream comprising hydrogen and/or carbon monoxide.

In another embodiment of the present invention, the water is added to the reactor system at a point where at least part of the olefinic feedstock has undergone conversion to form aldehydes. This involves addition of the water at a point part of the way along the reaction environment. The water may be added at the start of or part of the way along any of the reaction zones. In the case where the reaction environment comprises one or more reactors, this may be achieved by addition of the water at a point part of the way along an individual reactor, or, where there is more than one reactor, at a point between two reactors. Due to the increased solubility of water in the aldehyde products in comparison to the olefinic feedstock, this embodiment has the advantage that more water may be added at this stage without risking flooding the reactor and quenching the reaction.

In a further embodiment, the water may be added to the output stream of the reactor system. Suitably, the water is added to the reactor system while the hydroformylation reaction is proceeding.

The feed stream for the hydroformylation process in step (c) comprises hydrogen, carbon monoxide, the first olefinic product fraction, catalyst, or catalyst components, optionally one or more recycle streams, also optionally one or more dopants and, optionally, water.

Suitable dopants include, but are not limited to, NaSH, $Na_2S$ and organic sulfur-containing additives including thiols, disulfides, thioethers and thiophenes.

The feed stream for the hydroformylation process may be introduced into the reaction environment as discreet feed streams or may be mixed together in any combination before entering the reaction environment.

Admixtures of promoters and/or stabilizers may also be included in the hydroformylation process in step (c). Thus, minor amounts of phenolic stabilizers such as hydroquinone and/or alkaline agents such as hydroxides of alkali metals, for example NaOH and KOH, may be added to the reaction environment.

The ratio of catalyst to the first olefinic product fraction to be hydroformylated is generally not critical and may vary widely. It may be varied to achieve a substantially homogeneous reaction mixture. Solvents are therefore not required. However, the use of solvents which are inert, or which do not interfere to any substantial degree with the desired hydroformylation reaction under the conditions employed, may be used. Saturated liquid hydrocarbons, for example, may be used as solvent in the process, as well as alcohols, ethers, acetonitrile, sulfolane, and the like. The molar ratio of catalyst to the first olefinic product fraction in the reaction zone of the hydroformylation process at any given instant is typically at least about 1:1000000, preferably at least about 1:10000, and more preferably at least about 1:1000, and preferably at most about 10:1. A higher or lower ratio of catalyst to the first olefinic product fraction may, however, be used, but in general it will be less than 1:1.

The organophosphine and/or organophosphite modified transition metal hydroformylation catalyst for use in step (c) may comprise a transition metal in complex combination with carbon monoxide and an organophosphine ligand and/or organophosphate ligand. By the term "complex combination"

as used herein, is meant a coordination compound formed by the union of one or more carbon monoxide and organophosphine and/or organophosphite molecules with one or more transition metal atoms. In its active form the suitable organophosphine and/or organophosphite modified transition metal hydroformylation catalyst contains one or more metal components in a reduced valence state.

Suitable organophosphine or organophosphite ligands include those having a trivalent phosphorus atom having one available or unshared pair of electrons. Any essentially organic derivative of trivalent phosphorus with the foregoing electronic configuration is a suitable ligand for the cobalt catalyst.

Organic radicals of any size and composition may be bonded to the phosphorus atom. For example the organophosphine or organophosphite ligand may comprise a trivalent phosphorus having aliphatic and/or cycloaliphatic and/or heterocyclic and/or aromatic radicals satisfying its three valencies. These radicals may contain a functional group such as carbonyl, carboxyl, nitro, amino, hydroxy, saturated and/or unsaturated carbon-to-carbon linkages, and saturated and/or unsaturated non-carbon-to-carbon linkages.

It is also suitable for an organic radical to satisfy more than one of the valencies of the phosphorus atom, thereby forming a heterocyclic compound with a trivalent phosphorus atom. For example, an alkylene radical may satisfy two phosphorus valencies with its two open valencies and thereby form a cyclic compound. Another example would be an alkylene dioxy radical that forms a cyclic compound where the two oxygen atoms link an alkylene radical to the phosphorus atom. In these two examples, the third phosphorus valency may be satisfied by any other organic radical.

Another type of structure involving trivalent phosphorus having an available pair of electrons is one containing a plurality of such phosphorus atoms linked by organic radicals. This type of a compound is typically called a bidentate ligand when two such phosphorus atoms are present, a tridentate ligand when three such phosphorus atoms are present.

The organophosphine and/or organophosphite modified transition metal hydroformylation catalyst to be used in step (c) can be prepared by a diversity of methods well known to those skilled in the art. A convenient method is to combine a transition metal salt, organic or inorganic, with the desired phosphine ligand, for example, in liquid phase followed by reduction and carbonylation. Suitable transition metal salts comprise, for example, transition metal carboxylates such as acetates, octanoates, etc. as well as transition metal salts of mineral acids such as chlorides, fluoride, sulfates, sulfonates, etc. as well as mixtures of one or more of these transition salts. The valence state of the transition metal may be reduced and the transition metal-containing complex formed by heating the solution in an atmosphere of hydrogen and carbon monoxide. The reduction may be performed prior to the use of the organophosphine modified transition metal hydroformylation catalysts or it may be accomplished in-situ with the hydroformylation process in the hydroformylation environment. Alternatively, the organophosphine modified transition metal hydroformylation catalysts can be prepared from a carbon monoxide complex of a transition metal.

Preferably, the first olefinic product comprises propylene and the aldehydes produced are at least normal butyraldehyde and iso-butyraldehyde.

In step (d) of the process at least part of the aldehydes as obtained in step (c) are separated into at least a first product fraction of aldehydes and a second product fraction of aldehydes. In step (d), the aldehydes as obtained in step (c) are separated into normal aldehydes and iso-aldehydes. This may be done using conventional distillation separation processes. Such processes are well known in the art and do not need further explanation. Preferably, the first product fraction of aldehydes as obtained in step (d) comprises iso-butyraldehyde and the second product fraction of aldehydes as obtained in step (d) comprises normal butyraldehyde. Preferably, the aldehydes are separated in a fraction enriched in normal aldehydes and depleted in iso-aldehydes and a fraction enriched in iso-aldehydes and depleted in normal aldehydes.

Preferably, first product fraction of aldehydes as obtained in step (d) comprises iso-butyraldehyde. More preferably the first product fraction of aldehydes comprises in the range of from 80 to 100 wt % of iso-butyraldehyde based on the aldehydes in the first product fraction of aldehydes.

Preferably, second product fraction of aldehydes as obtained in step (d) comprises normal butyraldehyde. More preferably the second product fraction of aldehydes comprises in the range of from 90 to 100 wt %, more preferably of from 99 to 100 wt %, even more preferably 99.9 to 100 wt % of normal butyraldehyde based on the aldehydes in the second product fraction of aldehydes.

In step (e), at least part of the aldehydes in the first and/or second product fraction of aldehydes as obtained in step (d) are hydrogenated to form a first product fraction of alcohols and/or a second product fraction of alcohols. Preferably, at least part of the first product fraction of aldehydes is hydrogenated and the first product fraction of alcohols as obtained in step (e) comprises an iso-alcohol, preferably iso-butyl alcohol.

In step (e) aldehydes as obtained in step (c) are hydrogenated with hydrogen to form alcohols. Depending on the aldehyde that is hydrogenated the alcohols formed are iso-alcohol and normal alcohol, preferably isobutyl-alcohol and normal butyl-alcohol.

The catalyst to be used in step (e) is metal-based catalyst. Suitable metals to be used include platinum, palladium, ruthenium, copper, chromium and nickel. Preferably, use is made in step (e) of a nickel-based catalyst. Preferably, step (e) is carried at a temperature in the range of from 100-150° C. and a pressure in the range of from 2-5 bar. Hydrogenation process are well known in the art and do not need further explanation.

Preferably, at least part of the second product fraction comprising aldehydes is withdrawn from the process as an aldehyde product, preferably comprising normal butyraldehyde.

Equally preferably, the aldehydes in the second product fraction comprising aldehydes are hydrogenated and at least part of the second product fraction comprising alcohols is withdrawn from the process as an alcohol product, preferably comprising normal butyl-alcohol.

In step (f) at least part of the first or second product fraction of alcohols are recycled to step (a). Depending on the desired aldehyde and/or alcohol product either the iso alcohols or the normal alcohols are recycled. Any alcohols recycled to step (a) are subsequently converted at least in part back to propylene. This propylene may be used as part of the first olefinic product to produced further aldehydes and optionally alcohols. Preferably, at least part of the first product fraction of alcohols, which comprises isobutyl-alcohol is recycled to step (a). More preferably, the entire first product fraction of alcohols which comprises isobutyl-alcohol is recycled to step (a).

The process according to the present invention integrates an OTO process for the production of olefins, in particular propylene, and a subsequent hydroformylation respectively hydroformylation/hydrogenation process for converting the propylene to butyraldehyde and butanol. Typically, the hydroformylation respectively hydroformylation/hydrogenation process produces a mixture of aldehydes or alcohols comprising more than one isomers of the aldehydes or alcohol such as in case of butyraldehyde, normal butyraldehyde and iso-butyraldehyde and in the case of butanol, normal butyl-alcohol and isobutyl-alcohol. A particular advantage of this integration is that the undesired isomer(s) of the aldehyde or alcohol may be recycled back, i.e. in the case of the aldehyde after hydrogenation to the corresponding alcohol, to the OTO process to be converted at least in part back to propylene. As such it is possible to produce essentially only the desired aldehyde or alcohol isomer. Due to the recycle of the undesired isomer it is not necessary that the hydroformylation respectively hydroformylation/hydrogenation process produces an aldehyde or alcohol mixture that is enriched in the desired aldehyde or alcohol, allowing a much broader and economic choice in possible hydroformylation respectively hydroformylation/hydrogenation processes and catalyst.

A further advantage of the integrated process according the invention is that part of the alcohol, in particular butanol, recycled back to step (a) is converted into ethylene. As the butanol was produced, via butyraldehyde from propylene, part of the propylene is converted to further ethylene, which is a valuable chemical feedstock.

The invention will be further described by way of the following non-limiting example.

EXAMPLE

Two catalysts, comprising 40 wt % zeolite, 36 wt % kaolin and 24 wt % silica were tested to show their ability to convert an isobutyl-alcohol-containing feedstock to an olefinic product. To test the catalyst formulations for catalytic performance, the catalysts were pressed into tablets and the tablets were broken into pieces and sieved. In the preparation of the first catalyst sample ZSM-23 zeolite powder with a silica to alumina molar ratio (SAR) 46, and ZSM-5 zeolite powder with a SAR of 80 were used in the ammonium form in the weight ratio 50:50. Prior to mixing the powders, the ZSM-5 zeolite powder was treated with phosphorus, resulting in a catalyst that has only one zeolite pre-treated with phosphorus. Phosphorus was deposited on a ZSM-5 zeolite powder with a silica-to-alumina ratio of 80 by means of impregnation with an acidic solution containing phosphoric acid to obtain a ZSM-5 treated zeolite powder containing 2.0 wt % P. The ZSM-5 powder was calcined at 550° C. Then, the powder mix was added to an aqueous solution and subsequently the slurry was milled. Next, kaolin clay and a silica sol were added and the resulting mixture was spray dried wherein the weight-based average particle size was between 70-90 μm. The spray dried catalysts were exposed to ion-exchange using an ammonium nitrate solution. Then, phosphorus was deposited on the catalyst by means of impregnation using acidic solutions containing phosphoric acid ($H_3PO_4$). The concentration of the solution was adjusted such to impregnate 1.0 wt % of phosphorus on the catalyst. After impregnation the catalysts were dried at 140° C. and were calcined at 550° C. for 2 hours. The final formulated catalyst thus obtained is further referred to as catalyst 1.

Another formulated catalyst was prepared as described herein above for catalyst 1, with the exceptions that only ZSM-5 with a SAR of 80 was used and which was not treated with phosphorus prior to spraydrying. The concentration of the phosphorus impregnation solution was adjusted such to impregnate 1.5 wt % of phosphorus on the catalyst formulation. The final formulated catalyst thus obtained is further referred to as catalyst 2.

The phosphorus loading on the final catalysts is given in Table 1 as wt % of elemental phosphorus in any phosphor species, based on the total formulated catalyst, and was determined by elemental analysis. The amount of phosphorus is based on the elemental weight of phosphorus (which does not need to be in elemental form though) and not on the total weight of phosphorus species present. This may be determined by elemental analysis and is also referred to as elemental phosphorus loading.

A stream of isobutyl-alcohol, comparable to an isobutyl-alcohol stream obtainable from a hydroformylation process, was provided. The isobutyl-alcohol in the presence and absence of methanol or methanol and butene-1 was reacted over the catalysts which were tested to determine their selectivity towards olefins, mainly ethylene and propylene. For the catalytic testing, a sieve fraction of 60-80 mesh was used. Prior to reaction, the molecular sieves were treated ex-situ in air at 550° C. for 2 hours.

The reaction was performed using a quartz reactor tube of 1.8 mm internal diameter. The molecular sieve samples were heated in nitrogen to the reaction temperature and a mixture consisting of 3 vol % butene-1, 6% vol % methanol balanced in $N_2$ was passed over the catalyst at atmospheric pressure (1 bar). In another experiment 3 vol % of isobutyl-alcohol, 6% vol % methanol balanced in $N_2$ was passed over the catalyst at atmospheric pressure (1 bar). In yet another experiment 3 vol % isobutyl-alcohol balanced in $N_2$ was passed over the catalyst at atmospheric pressure (1 bar). The Gas Hourly Space Velocity (GHSV) is determined by the total gas flow over the zeolite weight per unit time (ml·gzeolite$^{-1}$·h$^{-1}$). The gas hourly space velocity used in the experiments was 19000 (ml·gzeolite$^{-1}$·h$^{-1}$). The effluent from the reactor was analyzed by gas chromatography (GC) to determine the product composition. The composition has been calculated on a weight basis of all hydrocarbons analyzed. The composition has been defined by the division of the mass of specific product by the sum of the masses of all products. The effluent from the reactor obtained at several reactor temperatures was analyzed. The results are shown in Table 1. The ethylene and propylene obtained are then subjected to the hydroformylation process. Iso-butyraldehydes obtained hydroformylation process are hydrogenated to isobutanol. This obtainable isobutanol is comparable to the isobutanol provided in this example.

It will be clear from the table 1 that the isobutanol is conveniently recycled to an OTO process to be converted to propylene, which may subsequently be used as a feed to a hydroformylation process. In addition, ethylene may formed by the conversion of isobutanol in an OTO process.

TABLE 1

| Catalyst | Feed | Vol % | Temp ° C. | C2= wt % | C3= wt % | C4 total wt % | C5 total wt % | C6 and heavier wt % | LE wt % | C4 sat/C4 total wt/wt |
|---|---|---|---|---|---|---|---|---|---|---|
| Catalyst 1 | C4=/MeOH/iC4OH | 0/0/3 | 575 | 8.37 | 22.81 | 64.73 | 2.86 | 1.15 | 0.09 | 1.36 |
| Catalyst 1 | C4=/MeOH/iC4OH | 0/6/3 | 575 | 17.07 | 50.97 | 27.62 | 2.02 | 2.15 | 0.17 | 2.39 |
| Catalyst 1 | C4=/MeOH/iC4OH | 3/6/0 | 575 | 16.07 | 52.81 | 26.81 | 1.95 | 2.06 | 0.29 | 1.72 |
| Catalyst 2 | C4=/MeOH/iC4OH | 0/0/3 | 575 | 12.91 | 32.65 | 49.65 | 2.05 | 2.48 | 0.25 | 3.01 |
| Catalyst 2 | C4=/MeOH/iC4OH | 0/6/3 | 575 | 19.56 | 50.53 | 23.91 | 1.74 | 3.70 | 0.55 | 4.09 |
| Catalyst 2 | C4=/MeOH/iC4OH | 3/6/0 | 575 | 18.16 | 51.93 | 23.62 | 1.63 | 3.88 | 0.77 | 2.64 |
| Catalyst 1 | C4=/MeOH/iC4OH | 0/0/3 | 525 | 8.30 | 30.58 | 52.70 | 5.64 | 2.75 | 0.03 | 2.72 |
| Catalyst 1 | C4=/MeOH/iC4OH | 0/6/3 | 525 | 13.73 | 49.31 | 28.41 | 4.08 | 4.41 | 0.05 | 4.24 |
| Catalyst 1 | C4=/MeOH/iC4OH | 3/6/0 | 525 | 13.16 | 50.98 | 27.91 | 3.97 | 3.95 | 0.04 | 2.93 |
| Catalyst 2 | C4=/MeOH/iC4OH | 0/0/3 | 525 | 13.16 | 41.77 | 37.70 | 3.62 | 3.57 | 0.17 | 5.08 |
| Catalyst 2 | C4=/MeOH/iC4OH | 0/6/3 | 525 | 16.76 | 49.29 | 24.70 | 3.33 | 5.53 | 0.39 | 5.77 |
| Catalyst 2 | C4=/MeOH/iC4OH | 3/6/0 | 525 | 15.94 | 50.68 | 24.54 | 3.11 | 5.15 | 0.58 | 4.09 |

The which is claimed is:

1. A process for the production of aldehydes and/or alcohols, which process comprises the steps of:
   (a) reacting an oxygenate and/or olefinic feed in a reactor in the presence of a molecular sieve catalyst to form an effluent comprising olefins, comprising propylene;
   (b) separating the effluent comprising olefins as obtained in step (a) into at least a first olefinic product fraction comprising propylene and a second olefinic product fraction;
   (c) subjecting at least part of the first olefinic product fraction as obtained in step (b) to a hydroformylation process to form aldehydes;
   (d) separating at least part of the aldehydes as obtained in step (c) into at least a first product fraction of aldehydes and a second product fraction of aldehydes;
   (e) hydrogenating at least part of the aldehydes in the first and/or second product fraction of aldehydes as obtained in step (d) to form a first product fraction of alcohols and/or a second product fraction of alcohols; and
   (f) recycling at least part of the first and/or second product fraction of alcohols obtained in step (e) to step (a).

2. The process according to claim 1, wherein the first product fraction of aldehydes as obtained in step (d) comprises iso-butyraldehyde and the second product fraction of aldehydes as obtained in step (d) comprises normal butyraldehyde.

3. The process according to claim 1, wherein at least part of the first product fraction of aldehydes is hydrogenated and the first product fraction of alcohols as obtained in step (e) comprises an iso-alcohol.

4. The process according to claim 1, wherein at least part of the first product fraction of alcohols is recycled in step (f) to step (a).

5. The process according to claim 4, wherein the entire first product fraction of alcohols is recycled to step (a).

6. The process according to claim 1, wherein at least part of the second product fraction comprising aldehydes is withdrawn from the process as an aldehyde product.

7. The process according to claim 1, wherein at least part of the second product fraction comprising alcohols is withdrawn from the process as an alcohol product.

8. The process according to claim 1, wherein the molecular sieve catalyst comprises a zeolite having at least 10-membered ring channels.

9. The process according to claim 8, wherein the zeolite is a zeolite of the MFI-type, the MEL-type, the MTT-type, the TON-type or any mixture thereof.

10. A process according to claim 1, wherein in step (c) the first olefinic fraction is contacted with carbon monoxide and hydrogen in the presence of a hydroformylation catalyst.

11. The process according to claim 10, wherein the hydroformylation catalyst comprises rhodium.

12. The process according to claim 1, wherein the oxygenate feed comprises methanol or dimethylether.

13. The process according to claim 1, wherein the reaction in step (a) is conducted at a temperature from 350 to 750° C.

14. The process according to claim 1, wherein the effluent comprising olefins as obtained in step (a) comprises ethylene and propylene.

15. The process according to claim 1, wherein the first olefinic product fraction as obtained in step (b) comprises in the range of from 50 to 100 wt % of propylene, based on the hydrocarbons in the first olefinic product fraction.

* * * * *